United States Patent
Gianna et al.

(10) Patent No.: US 7,438,886 B2
(45) Date of Patent: Oct. 21, 2008

(54) CHEMICAL-BIOLOGICAL PROCESS FOR THE REMOVAL OF $H_2S$ FROM A GAS

(75) Inventors: Roberto Gianna, Rome (IT); Umberto Barberini, Rome (IT); Mario Galileo Valdiserri, Rome (IT); Francesco Crescenzi, Rome (IT); Andrea Robertiello, Rome (IT)

(73) Assignee: Enitechnologie S.p.A., San Donato Milanese (IT)

( * ) Notice: Subject to any disclaimer, the term of this patent is extended or adjusted under 35 U.S.C. 154(b) by 296 days.

(21) Appl. No.: 10/538,925

(22) PCT Filed: Dec. 4, 2003

(86) PCT No.: PCT/EP03/13798

§ 371 (c)(1),
(2), (4) Date: May 30, 2006

(87) PCT Pub. No.: WO2004/056454

PCT Pub. Date: Jul. 8, 2004

(65) Prior Publication Data

US 2006/0251571 A1    Nov. 9, 2006

(30) Foreign Application Priority Data

Dec. 20, 2002  (IT) .......................... MI2002A2705

(51) Int. Cl.
*B01D 53/52* (2006.01)
*C01B 17/04* (2006.01)
*C01B 17/05* (2006.01)

(52) U.S. Cl. .............. 423/573.1; 423/576.4; 423/576.5; 423/DIG. 17

(58) Field of Classification Search .............. 423/573.1, 423/576.4, 576.5, DIG. 17
See application file for complete search history.

(56) References Cited

U.S. PATENT DOCUMENTS 1,701,825 A * 2/1929 Seil ............................ 435/266

(Continued)

FOREIGN PATENT DOCUMENTS

| EP | 0 811 416 | 12/1997 |
|---|---|---|
| WO | 92/17401 | 10/1992 |

OTHER PUBLICATIONS

U.S. Appl. No. 10/538,925, filed Jun. 13, 2005, Gianna, et al.
U.S. Appl. No. 08/855,445, filed May 13, 1997, Gianna, et al.

*Primary Examiner*—Timothy C Vanoy
(74) *Attorney, Agent, or Firm*—Oblon, Spivak, McClelland, Maier & Neustadt, P.C.

(57) ABSTRACT

The present application relates to a process for removing hydrogen sulfide $H_2S$ from a gas (1) by contacting said gas with a liquid solution (2) containing ferric sulfate in an absorption column (RC). Ferric sulfate and $H_2S$ react at room temperature and at a pressure ranging from 1 to 1.2 atm. Ferric ions being reduced to two-valent iron and sulfide oxidised to elemental sulfur. The liquid (4) coming out of the absorption column is filtered in two steps, the retentate (6, 8) comprising elemental sulfur, the filtrate (5, 7) containing the iron ions. The filtrate is sent to a bioreactor (RB) for regeneration, i.e. oxidation of iron to $Fe^{3+}$ by means of *thiobacillus ferroxidans* and air injection (10). The regenerated solution is reused in the absorption column (RC). The process faces the problems relating to the alignment between the chemical step and the biological step in order to obtain a process which can stably run continuously.

6 Claims, 1 Drawing Sheet

U.S. PATENT DOCUMENTS

| | | | |
|---|---|---|---|
| 3,218,252 A | * 11/1965 | Glover et al. | 210/611 |
| 4,931,262 A | * 6/1990 | Sonta et al. | 423/220 |
| 5,236,677 A | * 8/1993 | Torres-Cardona et al. | 423/230 |
| 5,508,014 A | 4/1996 | Rai | |
| 5,753,189 A | 5/1998 | Rehmat | |
| 5,843,382 A | 12/1998 | Rehmat | |
| 5,989,513 A | * 11/1999 | Rai | 423/573.1 |
| 6,056,934 A | * 5/2000 | Carlsen et al. | 423/522 |

* cited by examiner

CHEMICAL-BIOLOGICAL PROCESS FOR THE REMOVAL OF H$_2$S FROM A GAS

The present invention relates to a chemical-biological process for the desulfurization of gaseous streams containing H$_2$S.

More specifically, the present invention relates to a chemical/biological process for the desulfurization of gaseous streams containing H$_2$S capable of operating stably and effectively in continuous regime.

Hydrogen sulfide is a polluting gas which is found in nature, in natural gas and in biogas, but it is also produced in gaseous streams by the chemical industry, in oil refining and the gasification of carbon. It is also often present in the effluents of industrial plants.

The article "Rounding Up Sulfur" published in Chemical Engineering of February 1995 describes numerous chemical methods for the separation of this pollutant.

The most widely-used technologies for desulfurizing gaseous streams are based on the Claus reaction between hydrogen sulfide and sulfur dioxide to give elemental sulfur and water. This approach is widely used for a vast range of applications which require a high adaptation capacity to specific operating necessities, as recently described in the article: Recovery of Sulfur from Sour Gas: A Review of the technology; published by Environmental Progress in 2002 (vol. 21 Nr. 3).

Claus technologies require large investments, they cannot be applied directly to the treatment of natural gas and they are not normally used for gaseous streams containing quantities of sulfur lower than 15 t/day. In these cases redox technologies, which operate in liquid phase, are considered more advantageous.

Many of these technologies use the ferric ion as oxidizing agent of the sulfide ion for the generation of elemental sulfur. Once the reaction has been completed, the solid sulfur is separated by filtration or centrifugation and the ferric ion is re-obtained by catalytic oxidation with air, the whole process is described for example in "Gas industry assesses new ways to remove small amounts of H$_2$S, Oil & Gas Journal of May 23, 1994.

A very efficient catalytic oxidation system with air of the ferrous ion to the ferric ion exploits the capacity of *Thiobacilli*, in particular *Thiobacillus ferroxidans*, which are capable of accelerating, in an acid environment, the natural oxidation rate by about 500,000 times.

On the basis of these elements, right from the beginning of the twentieth century, attempts have been made to develop separation processes of H$_2$S based on the following reactions:

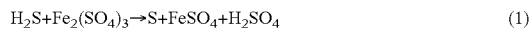

$$H_2S+Fe_2(SO_4)_3 \rightarrow S+FeSO_4+H_2SO_4 \quad (1)$$

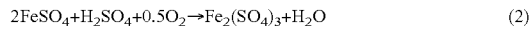

$$2FeSO_4+H_2SO_4+0.5O_2 \rightarrow Fe_2(SO_4)_3+H_2O \quad (2)$$

$$H_2S+0.5O_2 \rightarrow S+H_2O \quad \text{(overall reaction)}$$

Considerable advantages can be potentially obtained by exploiting the above reactions:

the chemical reaction (1) is almost instantaneous and can be carried out with relatively high concentrations of the iron ion, without the necessity of using organic complexing agents, if operating with acid pH values which limit the precipitation phenomena of the reagent in the form of hydroxides;

the biological reaction (2) takes place spontaneously at a temperature close to room value, it does not envisage the consumption of costly products as *T. ferroxidans* is a micro-organism which only requires carbon dioxide (present in the air) and simple mineral salts, for its own multiplication. There are no problems of sterility as *Thiobacilli* are the only micro-organisms which are capable of multiplying at strongly acid pH values, using only the energy obtained from the oxidation of the ferrous ion to the ferric ion;

the separation processes of H$_2$S based on the joint exploitation of the two reactions, are extremely versatile, as they can be used in almost all applicative contexts and are very flexible to changes, also sudden, in the composition of the gas to be treated.

In spite of these advantages, the development of technologies based on the exploitation of reactions (1) and (2) is hindered by the necessity of overcoming the following main problems:

the production of sulfur, in crystalline form, which can be easily separated from reaction (1), is critical for maintaining the continuity of the unitary operations, for minimizing the loss of the iron ion and obtaining a product with a sufficient purity for market demands;

the alignment of the two reactions is based on a very delicate equilibrium on which the stability of the continuative running of the two main unitary operations forming the process, depends. One of the critical parameters of this equilibrium consists, for example, of the pH which can vary only within a very narrow range, normally between 1.4 and 2.0. Below the minimum value, the activity of *T. ferroxidans* is inhibited; over the maximum value precipitation phenomena of the ferric ion are triggered;

another critical parameter consists of maintaining the correct concentrations of ammonium, phosphate, potassium and magnesium ions, necessary together with CO$_2$, for the multiplication of *T. ferroxidans*. The formation of insoluble precipitates of jarosites is known—under the operating conditions normally used for exploiting the reaction (2)—for example potassium [KFe$_3$(SO$_4$)$_2$(OH)$_6$], which subtract Fe$^{+3}$, NH$_4^+$, K$^+$ and OH$^-$ from the system, at the same time contributing to an acidification of the liquid stream (Anders B. Jensen & Colin Webb, Ferrous Sulphate Oxidation Using *T. ferroxidans* (1995) Progress Biochemistry 30, 225-236; C. Pogliani & E. Donati Immobilization of *T. ferroxidans*: importance of jarosites precipitation (2000) Progress Biochemistry 35, 997-1004);

the modest efficiency of the common oxidation systems of the ferrous ion to the ferric ion biocatalyzed by *Thiobacilli*. This creates economic and technological problems, for the practical use of reaction (2), of having to adopt reactors having considerable dimensions.

According to literature data, many technological approaches have been proposed, aimed at exploiting reactions (1) and (2) and overcoming or limiting the effect of the practical problems mentioned above.

The patent EP 220776, for example, describes a chemical-biological desulfurization process which exploits reactions (1) and (2) in which the bioreactor, where the ferric sulfate is regenerated, operates with micro-organisms in a suspended medium which are recovered from the solution containing oxidized iron with the use of ultra-filtration membranes, thus maintaining a high cellular concentration and at the same time obtaining sulfur with a higher degree of purity.

Patent EP 280750 describes a chemical-biological desulfuration process which exploits reactions (1) and (2), in which the bioreactor contains a solid carrier on which iron-oxidizing bacteria have been deposited, which operate in a submersed medium. In this way it is possible to raise the efficiency of the bioreactor, at the same time limiting the bacterial contamination of the sulfur produced. EP 280750 also describes examples for effecting the process in continuous, which however are limited to a period of three days and do not provide details on the operating procedure.

Patent EP 811416 describes a chemical-biological desulfurization process based on the exploitation of reactions (1) and (2), in which the oxidation of the ferrous sulfate takes place in a bioreactor containing a solid carrier covered by a biofilm of iron-oxidizing bacteria of the *Thiobacillus* type, which operate in an immersed medium (trickling-bed). The process enables a better productivity to be obtained (referring to g of $Fe^{2+}$ oxidized per h and per liter of the reactor), with respect to that obtained in the biotechnological processes described in the known art.

EP 811416 also describes the possibility of carrying out reaction (1) at temperatures higher than room temperature thus obtaining a more easily separable crystalline sulfur.

None of the documents cited, however, faces problems relating to compatibilization/alignment between the chemical step and the biological step with the final objective of obtaining a process for desulfurizing a gaseous fluid containing $H_2S$ which can be stably run in continuous regime and which, at the same time, is reliable, flexible and has a high separation capacity of the $H_2S$.

Furthermore, no document provides details on the continuous functioning of the integrated system consisting of the chemical step and the biological step.

A chemical-biological process has now been found for the desulfurization of gaseous streams containing $H_2S$ which overcomes the problems of compatibilization/alignment between the chemical step and the biological step and which can be run stably, in continuous regime, with reliability, flexibility and a high separation capacity of the $H_2S$.

In accordance with this, an object of the present invention relates to a continuous process for the desulfurization of gaseous streams containing $H_2S$, comprising, according to the scheme provided in FIG. 1:

(a)—feeding to the bottom of an absorption column (RC) operating at room temperature and at a pressure normally ranging from 1 to 1.2 Atm, a gaseous stream (1) containing $H_2S$ at concentrations ranging from 10 ppmv to 99% vol/vol;

feeding to the same column a liquid stream (2), removed from the bottom of a biological reactor (RB), containing a solution of ferric/ferrous sulfate with total concentration ranges of iron of 0.1-0.5 M and molar ratios within the range (100:0 up to 60:40), with pH values within the range of 1.40-1.90;

streams 1 and 2 being fed in such quantities that the ratio in moles between the $H_2S$ and ferric iron ranges from 1:20 to 1:4;

(b)—extracting the gaseous stream (3), purified of $H_2S$, from the head of the absorption column RC, together with a stream (4) consisting of a solution of ferrous/ferric sulfate in which the concentration of the $Fe^{2+}$ ion ranges from 0.025 to 0.15 M, in which elemental sulfur is suspended in the form of crystalline particles with an average particle size higher than 70 μm at concentrations within the range of 0.1-5 g/l;

(c)—feeding said stream (4) to a filtration system;

(d)—extracting from the filtration system a limpid stream (5) consisting of a ferric:ferrous sulfate solution in a molar ratio within the range of 80:20-40:60, at total iron concentrations ranging from 0.1-0.5 M and pH ranges of 1.90-1.50;

extracting a solid stream (6) with a sulfur content of 50-70% from the filtration system;

(e)—resuspending in a stirred reactor the solid stream (6) of raw sulfur in a quantity of water equal to the overall amount lost by evaporation from the process and feeding the suspension thus obtained to a filtration system;

(f)—extracting from the filtration system a limpid stream (7) consisting of a solution of ferric:ferrous sulfate and a solid (8) consisting of sulfur at 98-99.5% of purity;

(g)—feeding stream (9) obtained by mixing streams (5) and (7) containing ferrous sulfate, ammonium hydroxide and ammonium phosphate, to the top of the biological reactor (RB), consisting of a trickle-bed containing an acid-resistant carrier colonized by *Thiobacillus ferroxidans*, in the quantities necessary for maintaining the concentrations of the above salts within the ranges of 0.1-0.5 M, 1-10 mM, 0.2-2 mM, respectively;

(h)—feeding to the bottom of the biological reactor a gaseous stream (10) consisting of air or air enriched with $O_2/CO_2$.

The process, object of the present invention, allows the chemical step to be stably and effectively aligned with the biological step, for the regeneration of the ferrous ion to the ferric ion and, without the use of additives or flocculating agents, the sulfur produced, to be easily and efficiently separated. In practice, crystalline particles are obtained with an average particle size higher than 70 μm, with considerable simplifications of the sulfur separation section.

In particular, the biological reactor operates with adhered biomass under trickle-bed conditions, efficiently oxidizing the ferrous ion.

Furthermore, the formulation of the culture medium allows the pH to be regulated between the two steps, eliminating the risk of occlusions of insoluble precipitates on the biocatalytic carrier.

The process, object of the present invention, forms a "zero discharge" productive system, as it does not generate any type of effluent. In addition, the characteristic of the autotrophous strain allows an amount of $CO_2$ equal to 15 Kg/t of sulfur produced to be separated.

Figure 1:
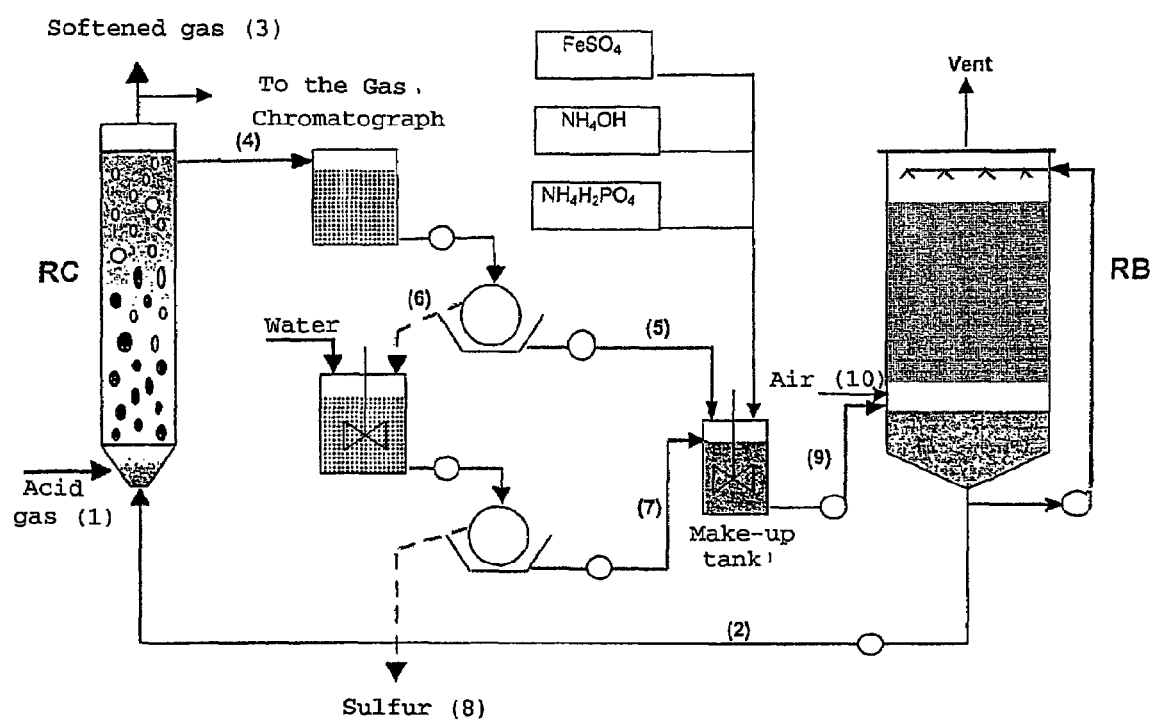
FIG. 1 illustrates an embodiment of the present invention.

More specifically, the process, object of the present invention, schematized in FIG. 1, operates in continuous and is based on four main unitary operations: chemical reaction, biological reaction, removal of sulfur and restoring of the process liquid (make-up).

The chemical absorption reactor (RC) consists of a bubble column which operates at room temperature, with pressure values normally ranging from 1 to 1.2 Atm, but which, with simple modifications, can also operate under pressure. At the head of the RC there is a level controller which regulates the flow-rate of the feeding pump of the oxidized substrate coming from RB in relation to the flow-rate of the extraction pump with which the sulfur suspension is transferred to the filtration section.

The flow of the gaseous stream (1) is regulated by a MF (Mass flow controller) and normally consists of $H_2S$, carbon dioxide, nitrogen, methane, other hydrocarbons and, possibly, traces of COS, $CS_2$, mercaptans. The feeding of the gas to RC is effected through one or more gas-spargers made of Teflon with pores of about 10 μm.

The ratio between the $H_2S$ and other gaseous components can range from 10 ppm to 99% ppm by volume. The flow and $H_2S$ content in said stream can be either fresh or recycled reagents, coming from the head of the chemical reactor RC.

The liquid phase (2), consisting of ferric:ferrous sulfate produced by the biological reactor RB, is sent to RC in equicurrent or in countercurrent, by means of a volumetric pump. The solution more specifically consists of ferric:ferrous sulfate with total iron concentration ranges of 0.1-0.5 M and molar ratios within the range (100:0 to 60:40), with pH values within the range of 1.90-1.40.

The composition of the softened gas leaving the RC section (3) is kept under control by means of gas-chromatographic analysis to mainly determine its content of residual $H_2S$, which normally varies from values close to zero to 10 ppmv.

The suspension of elemental sulfur which is formed in RC is maintained at a value of total suspended solids ranging from 0.1 to 5 g/l. The slurry (4) consisting of a solution of ferrous/ferric sulfate in which the concentration of the $Fe^{2+}$ ion ranges from 0.025 to 0.15 M, preferably 0.10 M, in which elemental sulfur is suspended, is removed and sent, by means of a volumetric pump, to the filtration system, for example of the vacuum-filter type.

The partially reduced limpid substrate (5), leaving the filtration system, consists of ferric:ferrous sulfate with total concentration ranges of the iron ion of 0.1-0.5 M and molar ratios $Fe^{3+}/Fe^{2+}$ within the range of 80:20 to 40:60, with pH values within the range of 1.90-1.50. The limpid substrate is sent, through the make-up reactor, to RB where it is regenerated.

The sulfur separation system generates a product, stream (6), with a total solid content of 50-70% and a degree of purity of 90-92%. A simple washing with water is sufficient to recover most of the ions present, obtaining a product (8) at 98-99.5% of purity.

The water and substrate recovered with the washing (7) is added to the make-up tank to compensate the loss of water by evaporation from the vacuum-filter and RB.

The biological reactor RB consists of a steel column of which 80% is filled with a solid acid-resistant carrier in a trickle-bed configuration. This configuration allows the contact to be maximized between the micro-organisms adhering to the inert carrier, the aqueous stream (containing ferrous sulfate) and the air—supplier of carbon dioxide (the sole carbon source for the growth of the micro-organism) and oxygen for the oxidation of the ferrous ion to ferric ion. The procedure used for the colonization of the catalytic carrier has already been described in a previous patent EP 811416 filed by the same applicant. The carrier is colonized by *Thiobacillus ferroxidans* which expresses its activity at strongly acid pH values (1.4-2.2); this extreme survival niche reduces the risk of competitors of the oxidation reaction, eliminating costly sterilization processes of the substrate. This makes it possible to operate on solutions with high concentrations of iron, maintaining a high separation efficiency of the $H_2S$ (reaction 1) and subsequent bio-oxidation (reaction 2).

The catalytic carrier is fed to the bottom by air or air enriched with $O_2/CO_2$ with a flow within the range of 0.8-16 vol/volume of reactor/h. The liquid stream is fed from above with flow-rates corresponding to hydraulic retention times ranging from 2 to 7 minutes. After wetting the carrier, the liquid stream is poured into an underlying container to be recycled. The reagents contained in the stream (2) can be either fresh or recycled reagents, coming from the RC section.

Furthermore, the stream 2 contains nutrients: nitrogen and phosphorous, which, together with the $CO_2$, form macronutrients, whereas the ferrous ion is the primary energy source. In the process, object of the present invention, the nitrogen source is ammonium hydroxide in a concentration varying from 1 to 10 mM, the phosphorous source is ammonium phosphate at a concentration varying from 0.2 to 2 mM. The formulation adopted allows the nutritional requirements of the micro-organism to be satisfied, minimizing the risk of the formation of insoluble jarosite precipitates, such as: $Kfe_3(SO_4)_2(OH)_6$ on the carrier.

The total iron ion concentration ranges normally used vary from 0.1 to 0.5 M, preferably 0.3 M and the molar ratios (ferric:ferrous) are within the range of 100:0 to 60:40, under these conditions the operative pH varies within the range of 1.90 to 1.50 units.

The feeding of the ferrous ion is ensured by stream 9, coming from the make-up section, after recovering the sulfur. The oxidized substrate (2) which serves to feed the chemical reactor RC, to complete the cycle, is removed from the bottom of the accumulation container.

By operating according to the process, object of the present invention, the operating costs are lowered, with a reduction in energy consumption, chemicals and labour necessary for the running of the process. Thanks to the considerable efficiency of the biological reactor and high concentration of the ferric ion used, the volumes of the two main RC and RB reactors are also minimized, thus reducing the process investment costs.

EXAMPLE 1

Desulfurization of Gas from Desorption on Amines

The experiment was carried out in continuous and programmed to reveal: the start-up phase, the operating flexibility of the bio-reactor with fluctuations in the concentration of $H_2S$ and finally, the stability of the system.

The start-up phase lasted about 15 days. In particular, with reference to FIG. 1, the gaseous stream 1 derives from a gaseous stream obtained from a plant using amines for the softening of natural gas with an $H_2S:CO_2$ composition equal to 60:40 vol/vol. The flow-rate of this stream was progressively increased by 270%, compatibly with the increase in the biological activity, the concentration of $H_2S$ being kept constant at 60% vol/vol. In the reactive absorption phase, the gaseous stream 1 is mixed with the liquid stream 2, containing ferric sulfate, in such quantities that the ratio in moles between $H_2S$ and the ferric ion ranges from 1:20 to 1:4, said ratio in moles normally being 1:10. These ratios usually lead to a variation of 5 to 25% in the percentage of ferrous ion in the stream 5, equal to an oscillation of 0.05-0.25 units of pH, normally restored by the biological activity. At the end of the start-up period there is a catalytic carrier capable of expressing productivity values of about 3.5 U (g of $Fe^{+3}$ produced $h^{-1}$ per liter of total volume of carrier).

A softened gaseous stream 3, with a residual content of $H_2S$ lower than 4 ppmv, is produced in the chemical reactor RC, normally using a height of the liquid seal not exceeding 200 cm.

After the start-up period with a productivity of 3.5 U, the stability of the system was determined for periods of not less than 4 weeks of continuous running. For this purpose, the following parameters were maintained constant: the charge and concentration of $H_2S$ at 60%; the molar ratio between the $H_2S$ in the gaseous stream 1, and the ferric sulfate, in the solution 2, equal to 6; the air flow to the biological reactor; the temperature of the aqueous medium between 24 and 35° C. Under these conditions, practically constant percentages of ferrous ion in streams 2 and 5 were recorded. More specifically, the percentage of ferrous ion and the pH value of stream 2 varied within the range of 8-12% and 1.75-1.82 units, respectively; the percentage of ferrous ion in stream 5, on the other hand, was kept within the range of 18-22% with pH values of 1.66-1.74. These limited oscillations can be attributed to the day/night thermal swing which influenced the operating temperature of the plant. Under these conditions, the residual concentration of $H_2S$ in stream 3 at the outlet of the absorber reaches and maintains the value of 4 ppmv.

The sulfur separation system ensured a raw product having a purity of 90-92% with a percentage of dry substance varying from 50 to 60%. A simple washing of the raw product, with deionized water, is sufficient to recover over 85% of ferrous sulfate soaked therein, producing sulfur having a purity of 98%.

The flexibility of RB with fluctuations of the ferrous ion charge was determined over a continuous operating period of not less than 4 weeks, cyclically varying the $H_2S$ charge and maintaining it constant for three days at two levels, one the double of the other. In particular, by varying the concentration of $H_2S$ in the in-flowing gas between 15 and 30%, the biological reactor can alternately operate in situations of hypo-feeding and hyper-feeding at 13.4 and 35.7 moles respectively Fe/h, $m^3$ of RB. At the lowest and highest level of the charge, the biological reactor RB operated on an average with percentages of oxidized substrate of 90-95% and 80-85%, with pH values of 1.85 and 1.75, respectively. Under the same Conditions, the chemical reactor RC allowed a percentage of ferric ion within the range of 70-75% and 60-65% respectively, to be reached, with pH values of 1.70 and 1.60 units. Under these conditions, the productivity of the biological reactor was established on an average at 1.5 and 3.0 U, respectively, with a low and high $H_2S$ charge.

The best process performances were tested by subjecting the system to increasing charges of $H_2S$, with the condition that the concentration of $H_2S$ in the softened gas of stream 3 remain equal to or lower than 4 ppmv. Under these conditions, a productivity on the biological reactor corresponding to 4.5 g of ferric ion produced $h^{-1}$ per liter of total carrier was recorded, which is much higher than other known processes specified in literature. With the maximum $H_2S$ charge, at a concentration in the in-coming gas of 60%, efficiency values of the chemical reactor of over 11.0 g of sulfur separated per liter of RC $h^{-1}$ were obtained, with separation percentages close to 100%, even with a liquid seal height reduced to 180 cm.

EXAMPLE 2

Desulfurization of Biogas

The stream (1) used consisted of: methane 81%, $CO_2$ 8%, $H_2S$ 8% and nitrogen 3%, the flow of gas treated was progressively increased between 23 vol/vol of RC/$h^{-1}$ and 91 vol/vol of RC/$h^{-1}$, operating at a pressure of 1.1 Atm and at room temperature. The height of the seal established in RC was 180 cm, with which a softened gas completely free of $H_2S$ was obtained. Under these operating conditions, the productivity of the biological reactor oscillates from 1 to 4 U (grams of ferric ion produced $h^{-1}$ per liter of total catalytic carrier). The percentage of ferrous ion recorded on the stream (2) varied from 5 to 20%, the pH values registered on stream (2) oscillated from 1.80 to 1.72 units.

EXAMPLE 3

Direct Desulfurization of Natural Gas

The natural gas is characterized by high flows with a low content of hydrogen sulfide, in this case stream (1) consisted of: methane 91%, $CO_2$ 6%, $H_2S$ 0.6% and nitrogen about 2%. The flow treated was constantly equal to 28 vol/vol(RC)/h, the operating pressure 1.2 Atm, operating at room temperature and with a liquid seal height of 130 cm. Under these hypo-feeding conditions, the biological reactor generated a stream (2) with a percentage of ferric ion within the range of 92-96% and pH values of around 1.85 units. The stream (5) expressed a percentage of ferric ion of 80 to 85% and pH values of 1.75-1.80. The softened gas of the outgoing stream (3) was free of $H_2S$.

The invention claimed is:

1. A continuous process for the desulfurization of gaseous streams containing $H_2S$, comprising, according to the scheme provided in FIG. 1:
    (a) feeding to the bottom of an absorption column (RC) operating at room temperature and at a pressure ranging from 1 to 1.2 Atm, a gaseous stream (1) containing $H_2S$ at concentrations ranging from 10 ppmv to 99% vol/vol; feeding to the same column a liquid stream (2), removed from the bottom of a biological reactor (RB), containing a solution of ferric/ferrous sulfate with total concentration ranges of iron of 0.1-0.5 M and molar ratios within the range (100:0 up to 60:40), with pH values within the range of 1.40-1.90;
    streams 1 and 2 being fed in such quantities that the ratio in moles between the $H_2S$ and ferric iron ranges from 1:20 to 1:4;
    (b) extracting the gaseous stream (3), purified of $H_2S$, from the head of the absorption column RC, together with a stream (4) consisting of a solution of ferrous/ferric sulfate in which the concentration of the $Fe^{2+}$ ion ranges from 0.025 to 0.15 M, in which elemental sulfur is suspended in the form of crystalline particles with an average particle size higher than 70 μm at concentrations within the range of 0.1-5 g/l;
    (c) feeding said stream (4) to a filtration system;
    (d) extracting from the filtration system a limpid stream (5) consisting of a ferric:ferrous sulfate solution in a molar ratio within the range of 80:20-40:60, at total iron concentrations ranging from 0.1-0.5 M and pH ranges of 1.90-1.50;
    extracting a solid stream (6) with a sulfur content of 50-70% from the filtration system;
    (e) resuspending in a stirred reactor the solid stream (6) of raw sulfur in a quantity of water equal to the overall amount lost by evaporation from the process and feeding the suspension thus obtained to a filtration system;
    (f) extracting from the filtration system a limpid stream (7) consisting of a solution of ferric:ferrous sulfate and a solid (8) consisting of sulfur at 98-99.5% of purity;
    (g) feeding stream (9) obtained by mixing streams (5) and (7) containing ferrous sulfate, ammonium hydroxide and ammonium phosphate, to the top of the biological reactor (RB), consisting of a trickle-bed containing an acid-resistant carrier colonized by *Thiobacillus ferroxidans*, in the quantities necessary for maintaining the concentrations of the above salts within the ranges of 0.1-0.5 M, 1-10 mM, 0.2-2 mM, respectively;
    (h) feeding to the bottom of the biological reactor a gaseous stream (10) consisting of air or air enriched with $O_2/CO_2$.

2. The process according to claim 1, wherein the chemical absorption reactor RC consists of a bubble column.

3. The process according to claim 1, wherein the concentration of the $Fe^{2+}$ ion in stream 4, is 0.10 M.

4. The process according to claim 1, wherein the solution of ferric:ferrous sulfate contained in stream (5) can be either fresh or recycled, coming from the RC section.

5. The process according to claim 1, wherein stream (5) contains ferrous sulfate at a concentration ranging from 0.025 to 0.15 M.

6. The process according to claim 1, wherein streams 1 and 2 are fed in such quantities that the ratio in moles between the $H_2S$ and ferric ion is 1:5.

* * * * *

UNITED STATES PATENT AND TRADEMARK OFFICE
CERTIFICATE OF CORRECTION

PATENT NO. : 7,438,886 B2 Page 1 of 1
APPLICATION NO. : 10/538925
DATED : October 21, 2008
INVENTOR(S) : Gianna et al.

It is certified that error appears in the above-identified patent and that said Letters Patent is hereby corrected as shown below:

On the title page, Item (73), the Assignee should read:

-- Assignee: Enitecnologie S.p.A., San Donato Milanese (IT) --

Signed and Sealed this

Sixth Day of January, 2009

JON W. DUDAS
*Director of the United States Patent and Trademark Office*